United States Patent [19]

Pinchuk

[11] Patent Number: 5,628,788
[45] Date of Patent: May 13, 1997

[54] SELF-EXPANDING ENDOLUMINAL STENT-GRAFT

[75] Inventor: Leonard Pinchuk, Miami, Fla.

[73] Assignee: Corvita Corporation, Miami, Fla.

[21] Appl. No.: 554,694

[22] Filed: Nov. 7, 1995

[51] Int. Cl.⁶ .................................................. A61F 2/06
[52] U.S. Cl. .................................. 623/1; 623/12; 606/194
[58] Field of Search ........................... 623/1, 2, 11, 12; 606/76–77, 194

[56] References Cited

U.S. PATENT DOCUMENTS

| | | |
|---|---|---|
| 1,920,495 | 8/1933 | Brown et al. . |
| 2,836,181 | 5/1958 | Tapp . |
| 2,977,839 | 4/1961 | Koch . |
| 3,095,017 | 6/1963 | Bleiler et al. . |
| 3,105,492 | 10/1963 | Jeckel . |
| 3,272,204 | 9/1966 | Artandi et al. . |
| 3,304,557 | 2/1967 | Polansky . |
| 3,317,924 | 5/1967 | Le Veen et al. . |
| 3,463,158 | 8/1969 | Schmitt et al. . |
| 3,479,670 | 11/1969 | Medell . |
| 3,485,234 | 12/1969 | Stevens . |
| 3,509,883 | 5/1970 | Diebelius . |
| 3,526,906 | 9/1970 | De Laszlo . |
| 3,562,820 | 2/1971 | Braun . |
| 3,580,289 | 5/1971 | James, Jr. . |
| 3,585,707 | 6/1971 | Stevens . |
| 3,626,947 | 12/1971 | Sparks . |
| 3,710,777 | 1/1973 | Sparks . |
| 3,730,835 | 5/1973 | Leeper . |
| 3,822,238 | 7/1974 | Blair et al. . |
| 3,868,956 | 3/1975 | Alfidi et al. . |
| 3,878,565 | 4/1975 | Sauvage . |
| 3,929,126 | 12/1975 | Corsaut . |
| 3,974,526 | 8/1976 | Dardik et al. . |
| 3,993,078 | 11/1976 | Bergentz et al. . |
| 4,044,404 | 8/1977 | Martin et al. . |

(List continued on next page.)

FOREIGN PATENT DOCUMENTS

| | | |
|---|---|---|
| 0587197 | 10/1991 | European Pat. Off. . |
| 1602513 | 1/1970 | France . |
| 3019996 | 12/1981 | Germany . |
| 1205743 | 9/1970 | United Kingdom . |
| 2015118 | 9/1979 | United Kingdom . |
| 2033233 | 5/1980 | United Kingdom . |
| 2077107 | 12/1981 | United Kingdom . |
| 2135585 | 3/1986 | United Kingdom . |
| WO88/00813 | 2/1988 | WIPO . |
| 8800813 | 2/1988 | WIPO ................................ 623/1 |
| WO91/12779 | 9/1991 | WIPO . |
| WO94/24961 | 11/1994 | WIPO . |

OTHER PUBLICATIONS

"A Study of the Geometrical and Mechanical Properties of a Self–Expanding Metallic Stent . . . " Jedwab et al, Jour. of Applied Biomaterials, Vo. 4, pp. 77–85 1993.

"Oesophageal Strictures" Didcott, Annals of the Royal Cllege of Surgeons of England, vol. 55, pp. 112–126, Aug. 1973.

Primary Examiner—John G. Weiss
Assistant Examiner—P. Zuttarelli
Attorney, Agent, or Firm—David P. Gordon

[57] ABSTRACT

A self-expanding endoluminal stent-graft includes a conventional wire stent and a tubular deformable material constructed of filaments and having a density and geometry such that when ends of the tubular material are pulled apart, the diameter of the tubular material decreases to one half to one tenth of its original diameter. The tubular deformable material is affixed to the interior or exterior of the self-expanding stent, preferably with an elastomeric adhesive. A biocompatible porous elastomeric liner is preferably affixed to the interior of the deformable member with an elastomeric adhesive. The tubular deformable member is preferably a PET mesh. The elastomeric adhesive is preferably a melt adhesive used in conjunction with a fibrous or porous layer which is applied to the exterior of the stent with a padding applicator to push the adhesive through the interstices of the stent onto the graft material. A second embodiment of the invention provides a bifurcated (e.g. Y-shaped) graft material.

20 Claims, 7 Drawing Sheets

U.S. PATENT DOCUMENTS

| | | |
|---|---|---|
| 4,086,665 | 5/1978 | Poirier . |
| 4,106,129 | 8/1978 | Carpentier et al. . |
| 4,130,904 | 12/1978 | Whalen . |
| 4,134,402 | 1/1979 | Mahurkar . |
| 4,140,126 | 2/1979 | Choudhury . |
| 4,164,045 | 8/1979 | Bokros et al. . |
| 4,173,689 | 11/1979 | Lyman et al. . |
| 4,193,138 | 3/1980 | Okita . |
| 4,323,071 | 4/1982 | Simpson et al. . |
| 4,355,426 | 10/1982 | MacGregor . |
| 4,441,215 | 4/1984 | Kaster . |
| 4,459,252 | 7/1984 | MacGregor . |
| 4,475,972 | 10/1984 | Wong . |
| 4,503,569 | 3/1985 | Dotter . |
| 4,583,968 | 4/1986 | Mahurkar . |
| 4,610,688 | 9/1986 | Silvestrini et al. . |
| 4,655,771 | 4/1987 | Wallsten . |
| 4,692,141 | 9/1987 | Mahurkar . |
| 4,731,073 | 3/1988 | Robinson . |
| 4,743,251 | 5/1988 | Barra . |
| 4,787,899 | 11/1988 | Lazarus . |
| 4,850,999 | 7/1989 | Planck . |
| 4,871,357 | 10/1989 | Hsu . |
| 4,875,480 | 10/1989 | Imbert . |
| 4,878,906 | 11/1989 | Lindemann et al. . |
| 4,895,561 | 1/1990 | Mahurkar . |
| 4,935,006 | 6/1990 | Hasson . |
| 4,954,126 | 9/1990 | Wallsten . |
| 5,026,377 | 6/1991 | Burton et al. . |
| 5,061,275 | 10/1991 | Wallsten et al. . |
| 5,064,435 | 11/1991 | Porter . |
| 5,078,720 | 1/1992 | Burton et al. . |
| 5,116,360 | 5/1992 | Pinchuk et al. ............................ 623/1 |
| 5,160,341 | 11/1992 | Brenneman et al. . |
| 5,188,593 | 2/1993 | Martin . |
| 5,197,978 | 3/1993 | Hess . |
| 5,201,757 | 4/1993 | Heyn et al. . |
| 5,235,966 | 8/1993 | Jamner . |
| 5,242,399 | 9/1993 | Lau et al. . |
| 5,279,561 | 1/1994 | Roucher et al. . |
| 5,290,295 | 3/1994 | Querals et al. . |
| 5,312,415 | 5/1994 | Palermo . |
| 5,330,500 | 7/1994 | Song . |
| 5,360,397 | 11/1994 | Pinchuk . |
| 5,383,892 | 1/1995 | Cardon et al. . |
| 5,395,390 | 3/1995 | Simon et al. . |
| 5,397,355 | 3/1995 | Marin et al. . |
| 5,405,378 | 4/1995 | Strecker . |
| 5,415,664 | 5/1995 | Pinchuk . |
| 5,433,723 | 7/1995 | Lindenberg et al. . |
| 5,507,771 | 4/1996 | Gianturco ................................... 623/1 |
| 5,527,353 | 6/1996 | Schmitt ....................................... 623/1 |

SELF-EXPANDING ENDOLUMINAL STENT-GRAFT

BACKGROUND OF THE INVENTION

1. Field of the Invention

The invention relates to an implantable prosthesis. In particular, the invention relates to a self-expanding endoluminal graft material for use with a stent as a stent-graft. The invention is particularly suited for repairing the aortic artery and daughter arteries, although it is not limited thereto.

2. State of the Art

Two types of implantable prostheses utilize tubular graft materials. These prostheses are known as vascular grafts and endoluminal stent-grafts. The endoluminal stent-graft typically includes tubular graft material which is affixed (usually with sutures) to the inside or outside of a woven metallic stent and is delivered to the damaged site via a catheter, whereas the vascular graft does not utilize a stent and is sutured in place using traditional open surgical techniques.

Vascular grafts are most often used to treat aneurysms and are typically made of tightly woven polyester (polyethylene terephthalate—"PET") fibers. PET fibers are chosen because they have a history of satisfactory long term use in the human body and because they can withstand relatively high hoop stress which is imparted by blood pressure in large diameter vessels. The fibers are tightly woven to limit the porosity of the graft in order to prevent blood loss during the initial stages of implantation and to facilitate preclotting with blood. As a result, these grafts are relatively non-compliant tubes which exhibit very little change in dimension when stressed in either the axial or radial directions. To further appreciate the lack of distensibility of these grafts, when using these types of grafts in a joint area, such as across a knee joint, these grafts must be mechanically and thermally crimped or corrugated in order that it be able to flex and change length when the recipient bends the knee joint. Such corrugations or crimps are also helpful during implantation of the graft so that the graft, if inadvertently cut too short, may be axially elongated during implantation. Although well-suited for open surgical procedures these bulky vascular graft constructions are difficult to use in an endoluminal application where the graft must be folded down within a deployment catheter.

An elastomeric vascular graft is disclosed in U.S. Pat. No. 4,475,972 to Wong, the complete disclosure of which is hereby incorporated by reference herein. As disclosed in Wong, polyurethane fibers are drawn from a viscous solution and extruded from a transversing spinnerette onto a rotating mandrel. As the filaments or fibers are wet as they are wound, they bond to each as they dry. The resulting graft is a porous tube having elastomeric properties. While the graft disclosed by Wong would appear to have many advantages, polyurethane grafts are not noted for their strength and it is believed that polyurethane may degrade over time. Therefore, it is believed that the prosthesis disclosed by Wong may be unsuitable for long term use in the human body and is not well suited for treating aneurysms. The graft taught by Wong may have greater elastomeric compliance than the vessel to which the graft is attached. This can result in an aneurism if a portion of the graft balloons after implantation. Thus, when treating aneurysms, the relatively non-compliant PET grafts are generally preferred.

My prior U.S. Pat. No. 5,163,951 discloses an improvement to the Wong graft wherein a PET mesh is adhered to the outside of the elastomeric Wong graft. The PET mesh is woven in a loose knit pattern (e.g. tricot or double tricot warp knit, atlas or modified atlas warp knit, jersey or double jersey patterns, etc.) to provide it with compliance. The PET mesh is adhered to the Wong graft material using an intermediate material (e.g. an aliphatic polycarbonate urethane) which has a melting point substantially lower than both the PET mesh and the Wong graft material. The intermediate material is placed between the PET mesh and the Wong graft material and the three component tubular structure is heated so that the intermediate material melts and mechanically bonds the PET mesh and Wong graft material during cooling. The compliance and porosity of the three component graft may be adjusted by adjusting the knitting parameters, the size and number of strands, and the angle at which the strands are drawn. The PET mesh gives the graft greater load bearing ability and also facilitates retention of sutures within the graft while maintaining some of the compliance of the Wong graft material.

Endoluminal stents are most often used to repair blood vessels affected by a variety of lesions which can compromise circulation of blood through the vessel, i.e. stenoses. A typical prior art stent, shown in FIGS. 1 and 2, is a metallic structure 10 made of braided wire 12 such as stainless steel, cobalt-chromium-nickel super alloys and combinations, co-extrusions or braised combinations of the above with tantalum, gold, platinum and the like. Stents are also made from memory alloys such as nitinol and the like. Typical stents are disclosed in U.S. Pat. Nos. 4,655,771 and 4,954,126 to Wallsten, the complete disclosures of which are hereby incorporated by reference, and in U.K. Patent Number 1,205,743 to Didcott, the complete disclosure of which is also hereby incorporated by reference. Generally, the wires 12 are braided with a large pick size, i.e. with relatively large interstices 14 between the wires, so that axial expansion of the stent causes a diametrical compression of the stent as shown in prior art FIG. 2. Most often the braiding and/or the metal chosen for the wires yields a resilient stent which is self-expanding. The ends of the stent are axially displaced during delivery so that the stent has a reduced diameter and can be easily located in the vasculature via a relatively small catheter. This is important since the location of the stent is typically severely narrowed by the stenosis. Upon locating the stent in the vessel, the stent is released so that the stent self-expands, as shown in prior art FIG. 1, and fixes itself to the interior of the vasculature thereby opening a passageway for blood circulation. While endoluminal stents have been used without any graft material, it is now preferred to use a graft material with the stent in order to prevent the growth of lesions through the picks (voids) in the stent and thus re-stenosis of the vessel.

The graft material most often used in endoluminal grafts is a PET or polytetrafluroethylene (PTFE) material which is folded to reduce its size and which is attached to one or both ends of a radially expandable stent by means of sutures. When the stent self-expands or is balloon expanded, the graft unfolds around the stent. A disadvantage of the non-elastic folded graft material is that it cannot be delivered through a small catheter. It is known to provide a porous endoluminal graft which is made of a spun matrix of polyurethane combined with a self-expanding stent. (See, Karo and Dereume et al., *Transactions of the 21st Meeting of the Society of Biomaterials*, Mar. 18–22, 1995, San Francisco, Calif., page 81.) The elastomeric polyurethane fibers allow the graft to compress with the stent and thereby permit delivery of the stent-graft through a relatively small catheter. However, as mentioned above polyurethane fibers may degrade over long term use in the human body.

While the primary use of endoluminal stents is to treat stenoses, stents are also sometimes used in conjunction with graft material to bridge aneurysms. The advantage of using a stent in bridging aneurysms is that the expanded stent helps to fix the graft in place, can eliminate the need for sutures, and may provide some additional resistance to hoop stress. As mentioned above, however, the preferred graft material for the treatment of aneurysms is relatively non-compliant tightly woven PET. In order to use this graft material, it must be folded, attached to the stent with sutures, and delivered through a relatively large catheter.

SUMMARY OF THE INVENTION

It is therefore an object of the invention to provide a graft material for use with an endoluminal self-expanding stent.

It is also an object of the invention to provide a self-expanding graft material for use with an endoluminal stent.

It is another object of the invention to provide a self-expanding graft material for use with an endoluminal stent where the graft material includes PET fibers.

It is a further object of the invention to provide a self-expanding PET graft material for use with an endoluminal stent wherein the graft material and the stent are attached to each other without sutures.

Another object of the invention is to provide a stent-graft where the graft and stent are intimately adhered to each other and where the graft is self-expanding in tandem with the stent.

It is yet another object of the invention to provide a stent-graft which has enhanced biocompatability.

A further object of the invention is to provide a stent-graft which has improved patency.

It is still another object of the invention to provide a stent-graft which has improved hoop stress resistance.

Yet a further object of the invention is to provide a stent-graft which facilitates the grafting of a major vessel and two branches of the major vessel.

In accord with these objects which will be discussed in detail below, the self-expanding endoluminal stent-graft of the present invention includes a conventional self-expanding wire stent, and a tubular deformable material constructed of filaments and having a density and geometry such that when ends of the tubular material are pulled apart, the diameter of the tubular material decreases to one half to one tenth of its original diameter. According to one preferred aspect of the invention, the tubular deformable material is affixed to the interior of the stent with an elastomeric adhesive. According to another preferred aspect of the invention, a biocompatible porous elastomeric liner is affixed to the interior of the deformable member with an elastomeric adhesive. The tubular deformable member according to the invention is preferably a warp-knit comprised of PET fibers. A presently preferred embodiment of the deformable member for a ten millimeter diameter vessel is a PET mesh using seventy denier, thirty-four filament, false twist fiber which is knit in a double tricot pattern with twenty-seven courses per inch and six needles per side. The presently preferred elastomeric adhesive is a melt adhesive used in conjunction with a fibrous or porous layer which is applied to the exterior of the stent and applied with a padding applicator to push the adhesive through the interstices of the stent onto the graft material. Additional aspects of the invention include providing a second biocompatible porous elastomeric layer on the exterior of the stent, and providing a second stent interior of the graft material.

A second embodiment of the invention provides a stent with a partially bifurcated or Y-shaped graft material. The bifurcated embodiment of the invention is particularly useful in repairing a major vessel and two branch vessels. The bifurcation of the graft material may be achieved using zig-zag sutures preferably using radiopaque suture material.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
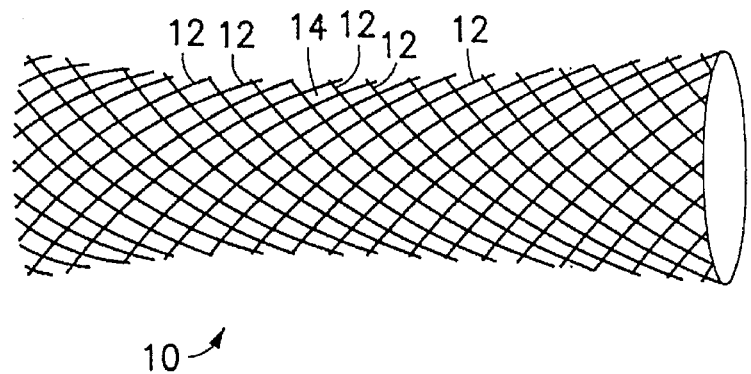
FIG. 1 is a side elevation view of a prior art stent in a radially expanded state.
Figure 2:
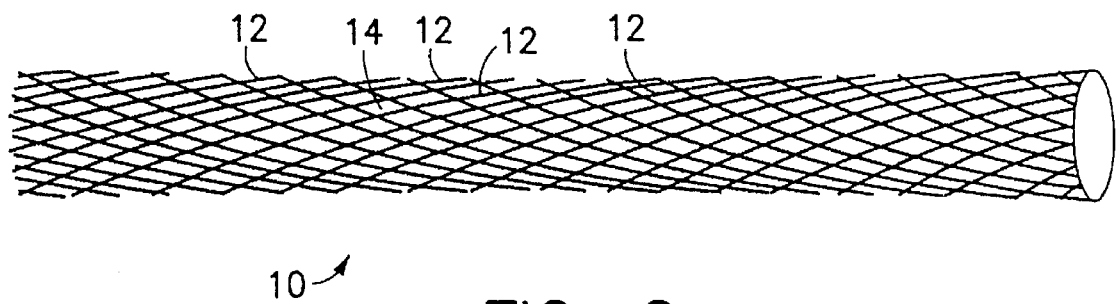
FIG. 2 is a side elevation view of the prior art stent of FIG. 1 in an elongated radially compressed state.
Figure 3:
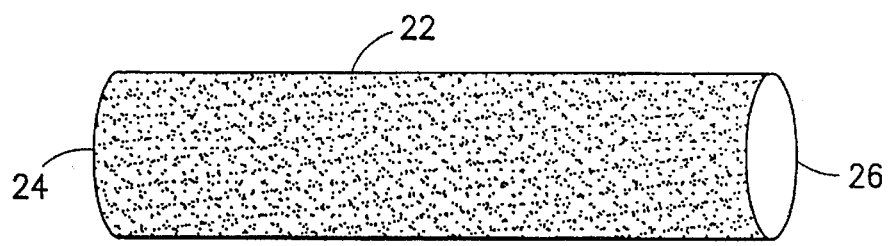
FIG. 3 is a side elevation view of a first embodiment of a self-expanding endoluminal graft according to the invention in a radially expanded state.
Figure 4:
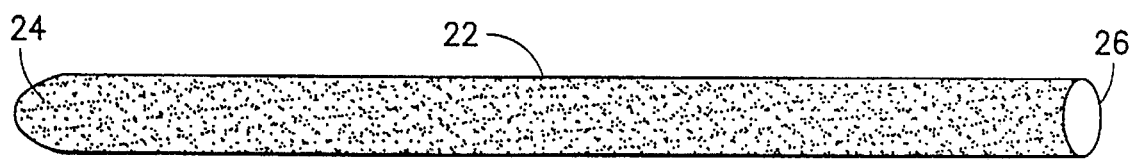
FIG. 4 is a side elevation view of the graft of FIG. 3 in an axially elongated and radially compressed state.
Figure 5:
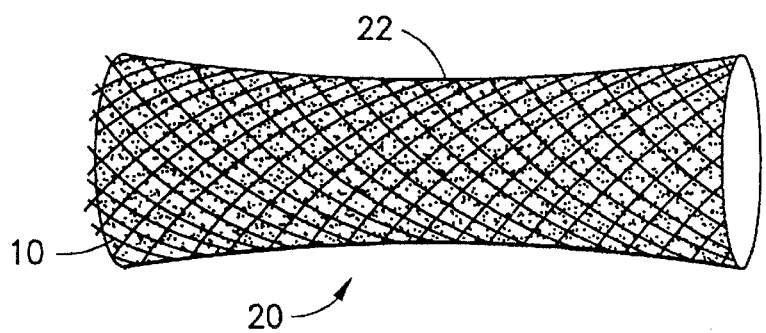
FIG. 5 is a side elevation view of the graft of FIG. 3 affixed to the stent of FIG. 1 in a radially expanded state.

Referring now to FIGS. 3 to 5, a self-expanding stent-graft 20, according to the invention includes a textile tube 22 which is axially and radially deformable. That is, when the ends 24, 26 are pulled apart, as shown in FIG. 4, the graft will compress radially as it is expanded axially. Preferably, when the ends 24, 26 are moved together, the graft will expand radially to the configuration shown in FIG. 3.

The textile tube 22 is preferably a warp-knit or atlas-knit of PET fibers. According to a presently preferred embodiment, the fibers are knitted using a double bar rochel knitting machine or a tubular warp-knit knitting machine. Alternatively, the tube 22 may be knit using a weft-knit where a single spool of fiber is knitted in a jersey stitch circular pattern. As a further alternative, the tube 22 may be braided in a manner similar to the stents disclosed by Didcott and Wallsten, i.e. as a one-over-one-under or two-over-two-under using PET fibers or the like. The braids can be made with single end filaments or with multiple end filaments and the cross-over points can then be sintered or glued such that the filaments do not unwind when the tube is cut or removed from the mandrel. As still a further alternative, the tube 22 may be constructed as a wound structure where filaments are wound back and forth along a rotating mandril and then sintered or glued at each cross-over point such that the filaments do not unwind when the tube is removed from the mandril.

According to the invention, the density of the textile material used to form the tube 22 is significant. Textile tubes which are knitted, woven, or braided with a high density will not have the expansion and compression deformability required by the invention. That is, if the pick size is too small, or there are too many filaments or ends present, the fibers will jam against each other when the ends of the tube are pulled apart and prevent radial compression of the tube. In a knitted textile tube, the picks are defined by stitches in the axial direction called courses and stitches along the circumference of the tube called wales. If the number of courses per inch is too high, the tube will not deform as described above. On the other hand, if the number of courses per inch is too low, the tube will be an open macroporous structure which will be ineffective as a graft since the structure will not prevent blood from flowing through the picks. Similarly, if the number of wales per inch is too low, the graft will not seal blood flow. If the number of wales per inch is too high, the graft will dilate with time. The number of picks per square inch is approximately equal to the product of the number of courses per inch and the number of wales per inch. While the number of courses per inch chosen according to the invention is largely independent of the dimensions of the graft, the number of wales per inch is directly related to the diameter of the graft.

It has been discovered that a textile tube 22 which is knitted from seventy denier filament PET should have between ten and forty courses per inch and between ten and forty wales per inch in order to be radially compressible to between one half and one tenth of its original diameter. The number of picks per square inch should therefore be between one hundred and one thousand six hundred; preferably between one hundred and four hundred.

Figure 6:
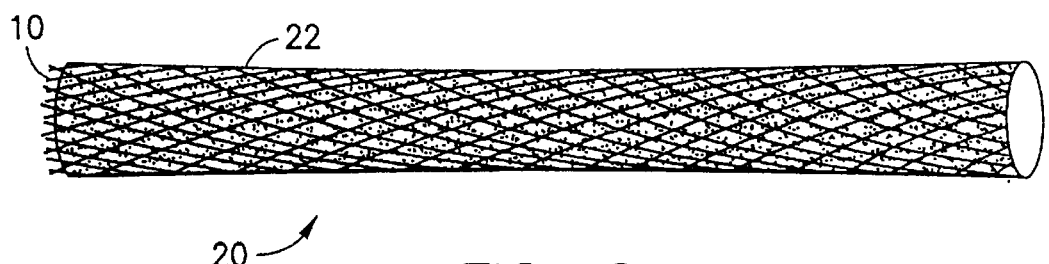
FIG. 6 is a side elevation view of the stent graft of FIG. 5 in an axially elongated and radially compressed state.
Figure 7:
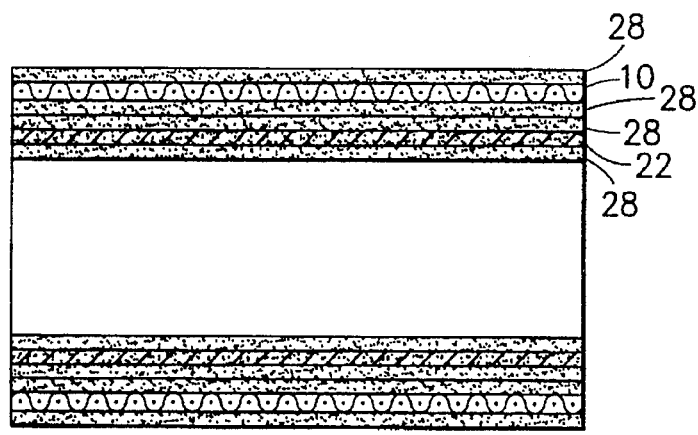
FIG. 7 is an enlarged cross sectional view of stent graft of FIGS. 5 and 6.

Referring now to FIGS. 5-7, the stent-graft 20 according to the invention includes a conventional self-expanding stent 10 which is affixed to the textile tube 22 with sutures or adhesive. According to a preferred embodiment of the invention, the textile tube 22 is attached to the stent 10 using an elastomeric adhesive 28. Suitable adhesives include polycarbonate urethanes such as described in U.S. Pat. No. 5,229,431, the complete disclosure of which is incorporated by reference herein. Silicone rubber adhesives may also be used. Silane priming agents may be used to enhance the bond of the adhesive. The adhesive 28 may be applied in several ways. The adhesive 28 may be applied to the stent 10 by dipping or spraying, after which the stent 10 is placed over the textile tube 22 and the adhesive is cured. Alternatively, the adhesive 28 may be applied to the textile tube 22 prior to placing it inside the stent 10. As another alternative, the stent 10 can be placed over the textile tube 22, after which the adhesive 28 is applied as a fibrous, or porous, layer over the stent 10 with the aid of a padding applicator whereby the adhesive 28 is pushed through the picks in the stent 10 and bonded to the textile tube 22. As still another alternative, either the stent 10 or the tube 22, or both, may be coated with a melt adhesive prior to placing the tube inside the stent. After assembling the stent and the textile tube, the stent-graft 20 is heated to melt the adhesive. The presently preferred embodiment of the invention utilizes a melt adhesive in combination with the padding technique described above. It is noted with respect to FIG. 7 (as well as FIGS. 8-12) that the adhesive 28 is shown as separate layers. However, those skilled in the art will appreciate that in many cases, the adhesive component of the stent-graft flows through the porous tube and macro-porous stent, especially after heating.

The invention will be better understood in conjunction with the following examples.

EXAMPLE 1

The self-expanding endoluminal stent-graft 20 shown in FIG. 7 includes a textile tube 22 which is knitted using seventy denier, thirty-four filament, false twist PET fibers having a melting point of approximately 240° C. The knit construction is a double tricot design having twenty-seven courses per inch, six needles per side. The tube 22 is expanded over a twelve millimeter mandril from a resting diameter of approximately four millimeters and coated with a thin fibrous (porous) layer of polycarbonate urethane 28 having a melting point of approximately 160° C. A Didcott-type stent 10 is provided. The stent 10 has twenty-four wire filaments, each being approximately 0.006 inches in diameter, which are braided one-over-one at an approximately 45° angle relative to the axis of the stent. The wires of stent 10 are spray coated with a thin layer of polycarbonate urethane 28, having a melting point of approximately 160° C., dissolved in dimethylacetamide solvent so that the polycarbonate urethane is approximately three and ten percent by weight. Both the stent 10 and the tube 22 are dried. The stent 10 is placed over the tube 22 and both are heated to approximately 160° C. such that the polycarbonate urethane 28 melts and bonds the stent 10 to the tube 22. The demolded stent-graft 20 can be pulled down from twelve millimeters in diameter to four millimeters in diameter without delamination of the tube 22 from the stent 10.

EXAMPLE 2

Seventy denier PET fiber is pulled through a bath of 10% polycarbonate urethane with a melting point of approximately 160° C. dissolved in dimethyl acetamide and then through an oven where the polyurethane is dried. The coated fiber is then re-spooled onto forty-eight carrier spools and braided on a braiding machine with a 90° pick angle on a twelve millimeter mandril. The stent 10 coated with polycarbonate urethane 28 as described in Example 1 is placed over the PET braid and both are heated to approximately 160° C. at which point the polyurethane melts and bonds the stent and the PET braid to each other at each crossover point in the braid. The demolded stent-graft can be pulled down from twelve millimeters in diameter to three millimeters in diameter without delamination of the PET braid from the stent 10.

EXAMPLE 3

The coated PET fiber described in Example 2 is placed on a transversing shuttle which reciprocates back and forth along the longitudinal axis of a twelve millimeter diameter rotating mandril. The speed of the shuttle and rotation of the mandril are controlled such that the angle at which the fiber crosses underlying fibers on the mandril is 45° as measured in respect to the longitudinal axis of the mandril. The twelve millimeter polycarbonate urethane coated stent described in Example 1 is placed on top of the wound structure and both are heated to 160° C. at which point the polyurethane component melts and bonds the stent to the wound structure and the PET fibers to each other. The assembly is then demolded and stretched longitudinally to demonstrate a reduction in diameter from twelve millimeters to three millimeters without delamination.

EXAMPLE 4

The warp-hit PET mesh 22 described in Example 1 is placed on a mandrel. A stent 10 is dip coated with a room-temperature vulcanizing silicone rubber adhesive. The wet stent 10 is placed over the mesh 22 on the mandril and the adhesive is cured at 100° C. in the presence of moisture for twenty minutes. The assembly is then demolded and stretched longitudinally to demonstrate a reduction in diameter from ten millimeters to three millimeters without delamination.

Figure 8:
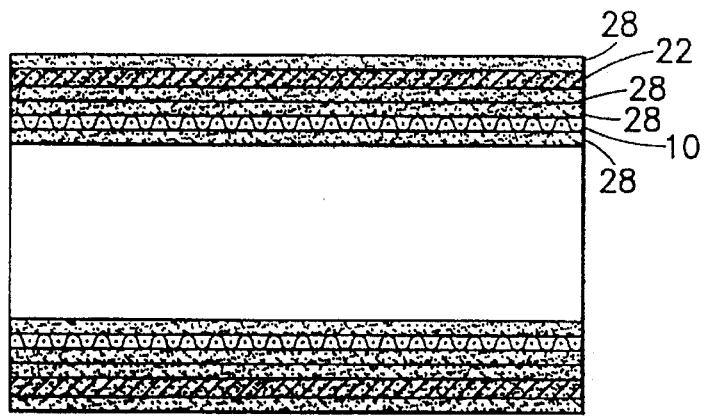
FIG. 8 is an enlarged cross sectional view of a first alternate embodiment of a stent graft according to the invention.

Each of the above Examples 1–4 has a cross-sectional structure substantially as shown in FIG. 7. However, those skilled in the art will appreciate that the relative locations of the stent 10 and the tube 22 may be reversed to form a stent-graft 220 as shown in FIG. 8 with the tube 22 located outside the stent 10. The stent-graft 220 has similar characteristics as described above. Further modifications of the basic structure of the invention are described in the Examples which follow.

EXAMPLE 5

Figure 9:
FIG. 9 is an enlarged cross sectional view of a second alternate embodiment of a stent graft according to the invention.

Referring now to FIG. 9, a stent-graft 320 according to the invention has an inner layer 30 of polycarbonate urethane having a melting point of approximately 240° C. The inner layer 30 is spun on a mandril into a non-woven tube or vascular graft in the manner described by U.S. Pat. No. 4,475,972 to Wong. An additional ten layers of fiber 32 are spun over the non-woven mesh 30 with a polycarbonate urethane having a melting point of approximately 160° C. The warp knit PET mesh 22 described in Example 1 is placed over the polycarbonate urethane 32 and an additional ten passes of polycarbonate urethane 32, having a melting point of approximately 160° C., are applied over the PET mesh 22. The stent 10 which is coated with polycarbonate urethane 28 as described in Example 1 is placed over the polycarbonate urethane 32 and the entire assembly is heated to approximately 160° C. at which point the layers 28 and 32 melt and bond the stent 10 to the mesh 22 and the mesh 22 to the polycarbonate tube 30. The assembly is demolded and stretched longitudinally to demonstrate a reduction in diameter from twelve millimeters to 4.5 millimeters without delamination.

EXAMPLE 6

Figure 10:
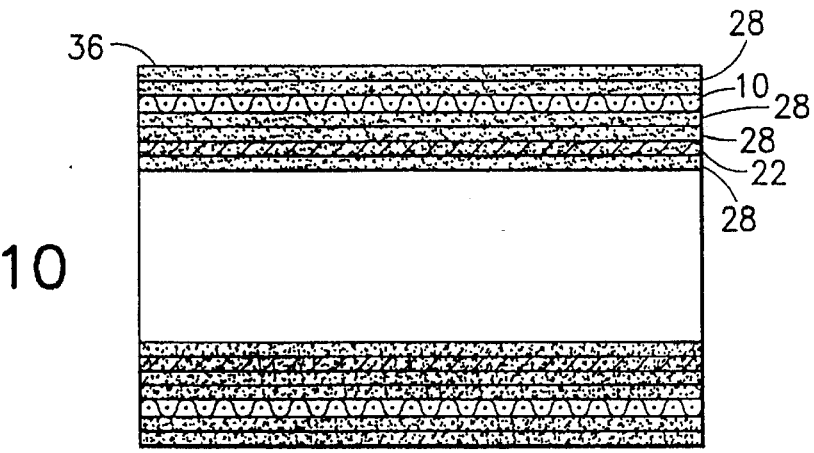
FIG. 10 is an enlarged cross sectional view of a third alternate embodiment of a stent graft according to the invention.

Turning now to FIG. 10, a stent-graft 420 according to the invention is manufactured according to Example 1 and further bonded by placing the stent-graft 20 (FIG. 7) on a mandril and coating the outside of the stent-graft with twenty passes of polycarbonate urethane fiber 30 using the Wong method. As the fibers are laid down, the fibers are padded through the picks in the stent 10 forming a bond between the polycarbonate urethane 36 and the stent 10 thereby increasing the bond strength of the stent 10 to the PET mesh 22. It will be appreciated that the additional outer polycarbonate urethane fiber layer 36 may be used in conjunction with Example 5 or in any embodiment wherein the stent 10 is the outermost layer.

EXAMPLE 7

Figure 11:
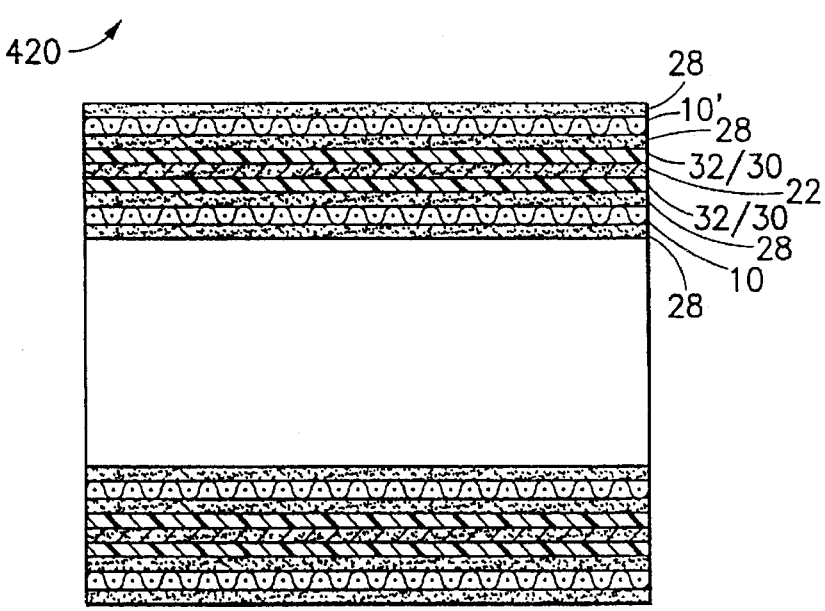
FIG. 11 is an enlarged cross sectional view of a fourth alternate embodiment of a stent graft according to the invention.

Still another stent-graft 520 according to the invention is shown in FIG. 11 where the stent-graft 520 includes the stent 10 which is coated with low melting point polycarbonate urethane 28 as described in Example 1. The coated stent is placed on a TEFLON-coated mandrel and twenty passes of polyurethane 32, having a melting point of approximately 160° C. is spun over the stent 10. Alternatively, a high melting point (e.g., 240° C.) polycarbonate urethane tube 30 such as taught by Wong may be spun over the stent 10. A PET sheath 22 is then placed over the covered stent or stent-graft, and twenty layers of 160° C. melting urethane 32, or alternatively, another non-woven tube such as taught by Wong is spun over the PET sheath 22. Another stent 10' coated with polycarbonate urethane 28 as per Example 1 is then placed over the coated sheath and the entire assembly heated in an oven at 160° C. for 15 minutes, then cooled and demolded. The resultant endoluminal stent-graft consists of, from the lumen outward, a stent 10, a non-woven polyurethane tube layer 30 (if utilized in lieu of a low temperature polyurethane 32), a PET tube 22, a second polyurethane layer 30 (again, if utilized in lieu of a low temperature polyurethane 32) and a second stent 10', with the layers bound together by polycarbonate urethane 28 and 32. The advantage of this embodiment is that if the polyurethane component were to degrade, the graft material remains essentially trapped between the wire stents.

EXAMPLE 8

Figure 12:
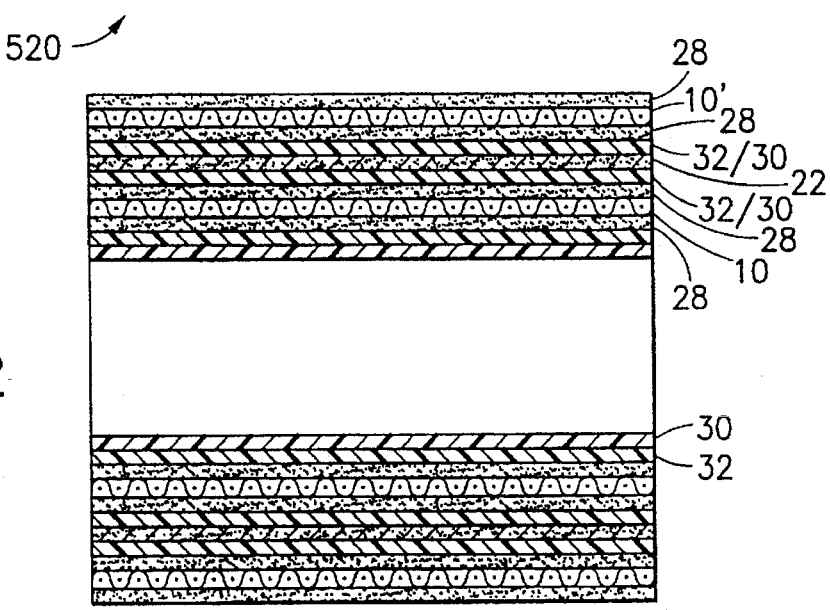
FIG. 12 is an enlarged cross sectional view of a fifth alternate embodiment of a stent graft according to the invention.

Turning now to FIG. 12, another stent-graft 620 according to the invention includes a polycarbonate urethane having a melting point of 240° C., which is spun on a mandrel into a non-woven tube or vascular graft 30 in the manner described by Wong. An additional ten layers of fiber 32 are spun over the non-woven mesh 30 with a polycarbonate urethane having a melting point of 160° C. The stent-graft 520 (FIG. 11) described in Example 7 (with the low or high melting point polyurethane 30, 32) is then placed over the fiber layer 32 and the entire assembly heated to 160° C. where the layers are bonded to one another. The resultant endoluminal stent-graft 620 includes, from the lumen outward, a porous polyurethane graft 30, a stent 10, another porous polyurethane graft 30 (when utilized in lieu of the low melting point polyurethane 32), a PET tube 22, and a second stent 10' with the layers bound together by low melting point polycarbonate urethane 28 and 32. The advantages of this embodiment are the same as Example 7. However, the polyurethane graft 30 on the inside of the device in this example, provides a good scaffold for tissue ingrowth and therefore a better flow surface than the PET or wire surfaces.

It should be noted that the inner stents 10 in Examples 7 and 8 need not be entirely coated with polyurethane melt adhesive 28, and that only the center or one end of the stent need be coated. Excessive adhesion between the inner stent and the outer layers may restrict the ability for the device to pull down in the event that there is a slight mismatch in geometry of the stents 10 and 10'. Partial bonding of the system allows for some mismatch in constructions by enabling slippage between the layers. It should be noted that the inner stent 10 in Example 7 and the inner stent 10 in Example 8 with the polyurethane graft adhered to it may be inserted into the stent grafts to form composite stent graft structures 520 and 620 after stent grafts are deployed into the body cavity. This permits deploying the composite endoluminal graft into the body cavity using smaller diameter introducers.

The self-expanding endoluminal stent-grafts described above are utilized by pulling the ends apart from each other with the aid of an "introducer" to radially compress the graft, by fitting the graft into a catheter, and by maneuvering the graft-containing catheter through a vessel to the site of implantation. Once the graft is located at the implantation site, it is deployed at this site by pushing it out through the end of the catheter and releasing the ends of the graft from the introducer so that the graft expands radially and bridges the underlying defects in the vessel.

As mentioned above, a second embodiment of the invention provides a bifurcated stent-graft which is particularly useful in repairing a major vessel and two branches of the major vessel, such as the aorta and the iliac arteries. A bifurcated graft according to the invention is shown in FIGS. 13 and 14, with bifurcated stent-grafts shown in FIGS. 15–18.

Figure 13:
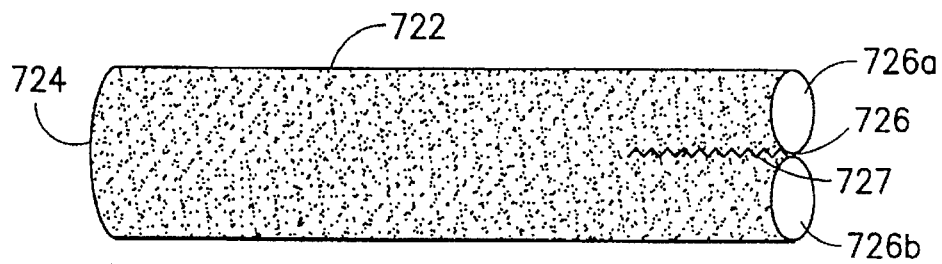
FIG. 13 is a view similar to FIG. 3 of a bifurcated graft according to the invention.
Figure 14:
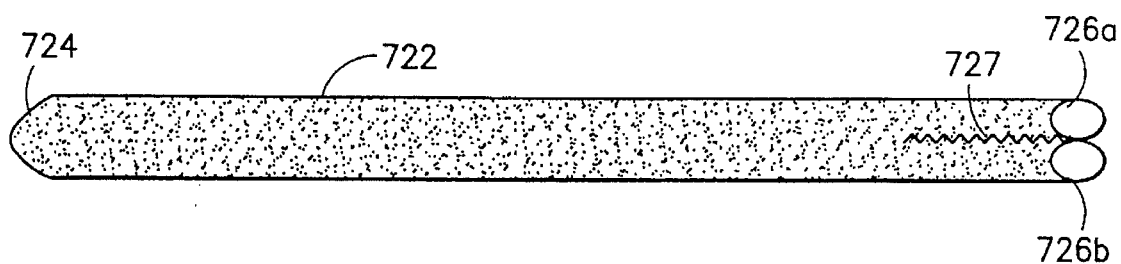
FIG. 14 is a view similar to FIG. 4 of the bifurcated graft of FIG. 13.

Turning now to FIGS. 13 and 14, a first bifurcated graft 720 according to the invention is constructed in a manner described by any one of Examples 1 through 8 and includes a warp-knit PET textile tube 722 as described above, which is radially compressible when its ends 724, 726 are pulled apart as shown in FIG. 14. According to the invention, one end 726 of the tube 722 is bifurcated with sutures 727 to create two lumens 726a, 726b. The sutures 727 are preferably sewn in a zig zag manner so as to allow axial elongation as shown in FIG. 14. Alternatively, the sutures 727 may be made from an elastomeric material such as a polycarbonate urethane. Still alternatively, individual sutures can be used instead of a continuous zig-zag suture to form the bifurcation and still allow axial elongation. As another alternative, an elastomeric adhesive such as a low melting point polycarbonate urethane or silicone rubber adhesive can be used to form the bifurcation; or the bifurcation can be formed by heat fusing the bifurcated area. It is desirous that the suture 727 forming the bifurcation be preferably made from a radiopaque material, such as barium or bismuth-filled PET, gold, tantalum, platinum or other radiopaque wire. Alternatively, the suture line can be painted with a radiopaque paint such as a tungsten, tantalum, or bismuth-filled silicone rubber to enable visualization of the bifurcation under fluoroscopy. The bifurcated tube 722 is affixed to one or more stents 10 as described in the Examples given above.

Figure 15:
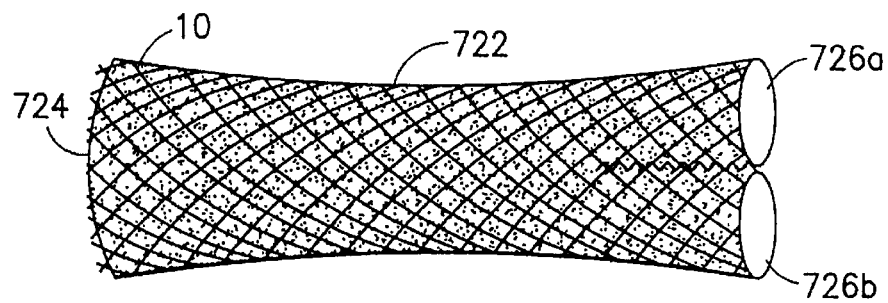
FIG. 15 is a view similar to FIG. 5 of the bifurcated graft of FIGS. 13 and 14 in conjunction with a stent.
Figure 16:
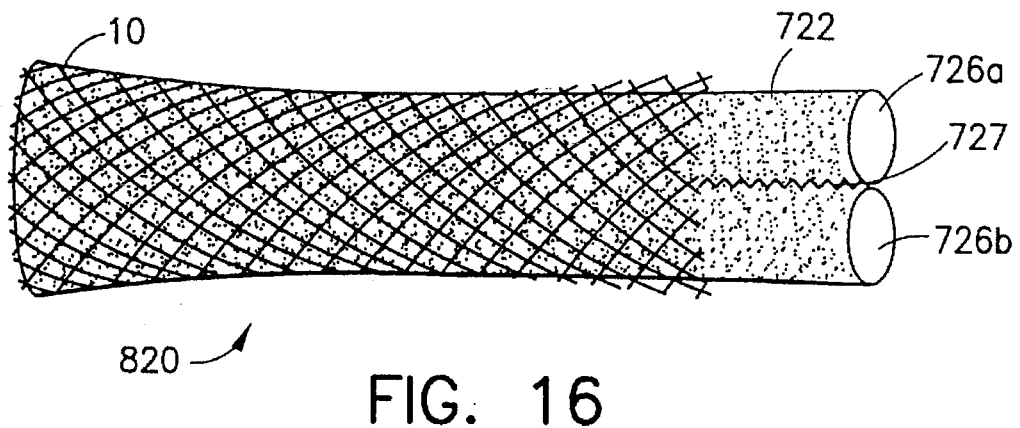
FIG. 16 is a view similar to FIG. 15 wherein the bifurcated portion of the graft extends beyond the stent.

As shown in FIG. 15, in the first version of this stent-graft embodiment of the invention, the entire tube 722 including the bifurcation is contained within the stent 10. Alternatively, and as shown in FIG. 16, a bifurcated graft 820 is provided wherein the bifurcated portion of the tube 722 defined by the sutures 727 is left uncovered by the stent 10.

Figure 17:
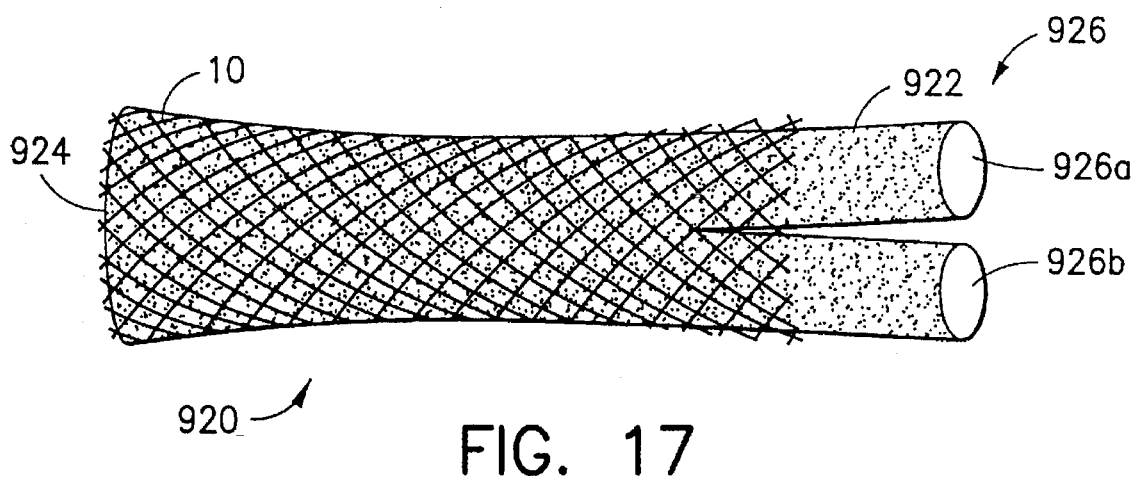
FIG. 17 a view similar to FIG. 16 wherein the bifurcated portion of the graft comprises two independent legs.

According to a second alternative, as shown in FIG. 17, a stent-graft 920 is provided wherein bifurcated tube 922 is formed with independent legs 926a, 926b at one end 926 of the tube. The legs are formed by providing parallel sutures and cutting between them. The tube 926 is affixed to one or more stents 10 as described above in the Examples. The bifurcated graft 920 may be formed with the legs 926a, 926b extending beyond the stent 10 as shown, or the entire tube 922 may be covered by one or more stents in the manner shown in FIG. 15, for example.

Figure 18:
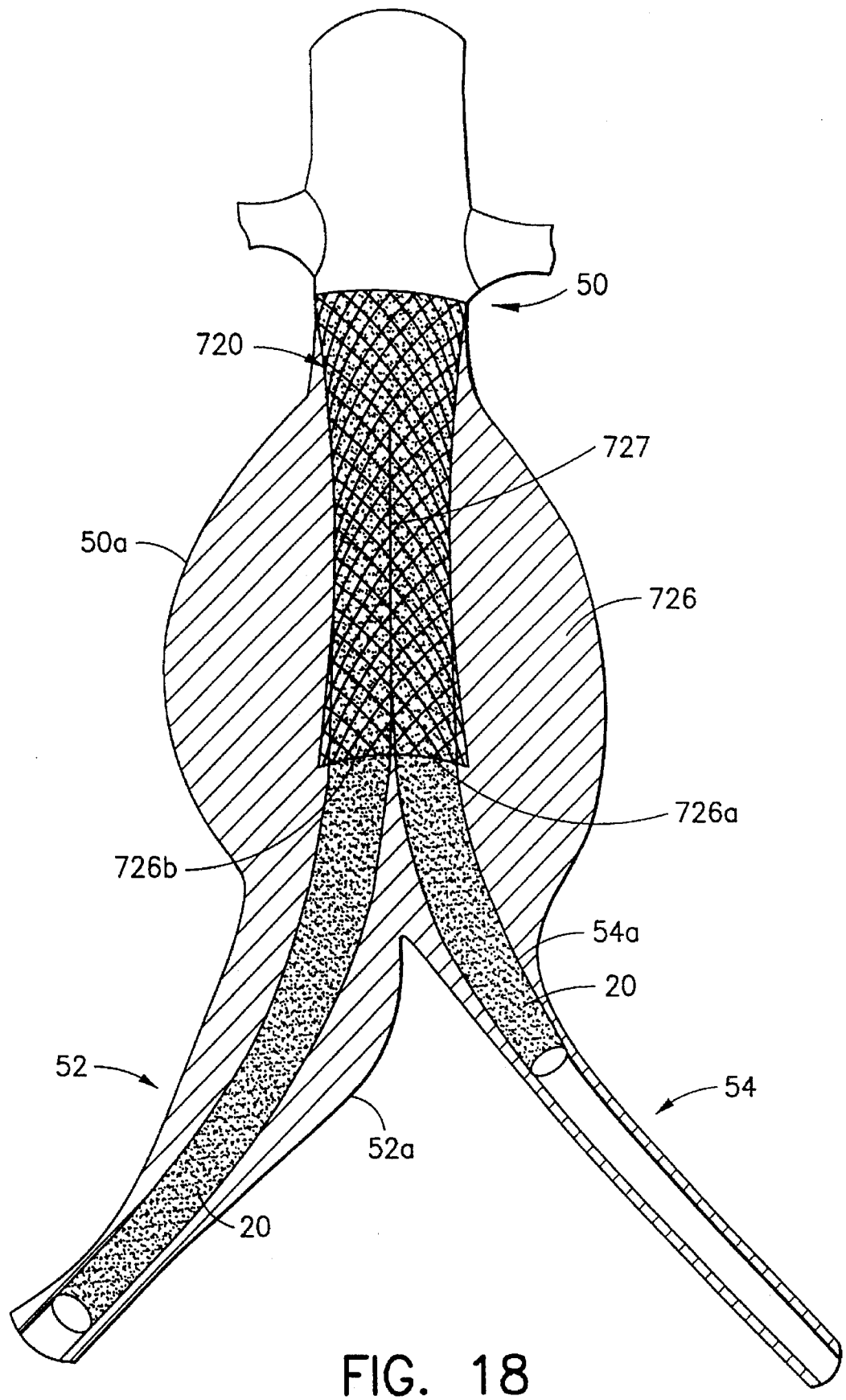
FIG. 18 is a schematic view of a bifurcated stent graft according to the invention bypassing the aortic artery and the iliac arteries.

FIG. 18 shows how a bifurcated stent-graft 720 according to the invention is useful in repairing an abdominal aortic aneurysm and iliac aneurysm. As shown in FIG. 18, the bifurcated graft 720 is located in the abdominal aortic artery 50 just above the iliac arteries 52, 54 with its bifurcated end 726 closest to the arteries 52, 54. The graft 720 effectively bypasses an aneurysm 50a in the aortic artery 50 and, as mentioned above, provides a radiopaque bifurcated guide to the iliac arteries 50, 52. Once the bifurcated graft 720 is deployed, two additional grafts 20 according to the invention, may be deployed in each of the iliac arteries 52, 54 to bypass aneurysms 52a, 54a. The additional grafts 20 are preferably deployed with the aid of guide wires (not shown) which are maneuvered into legs 726a, 726b of aortic trunk graft 720. The guide wires direct two introducers (not shown) into each iliac artery 52, 54 wherein the additional grafts 20 are deployed. The bifurcated legs 726a, 726b of the graft 720 provide separate fluid couplings for the two additional grafts 20 so that blood can flow from the aortic artery to both iliac arteries.

There have been described and illustrated herein several embodiments of a self-expanding endoluminal graft. While particular embodiments of the invention have been described, it is not intended that the invention be limited thereto, as it is intended that the invention be as broad in scope as the art will allow and that the specification be read likewise. Thus, while the endoluminal stent-grafts have been discussed in connection with vascular applications, the stent-grafts according to the invention can be used to graft other vessels such as biliary ducts, the esophagus, ureters, urethra, the trachea, the intestines, other visceral cavities and the like. In addition, the stent-grafts according to the invention can be constructed with larger or smaller diameters depending upon the intended application and size vessel to be grafted. It will therefore be appreciated by those skilled in the art that yet other modifications could be made to the provided invention without deviating from its spirit and scope as so claimed.

I claim:

1. A self-expanding endoluminal stent-graft, comprising:

a) a self-expanding wire stent having a geometry such that when ends of said self-expanding wire stent are pulled apart, the diameter of said self-expanding wire stent decreases to between approximately one half to approximately one tenth of the original diameter of said wire stent; and b) a tubular deformable textile material constructed of filaments and having a density and geometry such that when ends of said tubular deformable textile material are pulled apart, the diameter of said tubular deformable material decreases to between approximately one half to approximately one tenth of the original diameter of said tubular deformable material, wherein said tubular deformable material is arranged substantially coaxially with said self-expanding wire stent and is affixed to said self-expanding wire stent.

2. A self-expanding endoluminal stent-graft according to claim 1, further comprising:

c) an elastic adhesive between said tubular deformable textile material and said self-expanding wire stent, said tubular deformable textile material being affixed to said self-expanding wire stent by said elastic adhesive.

3. A self-expanding endoluminal stent-graft according to claim 1, wherein:

said tubular deformable textile material is a PET mesh.

4. A self-expanding endoluminal stent-graft according to claim 3, wherein:

said PET mesh is one of a warp-knit, atlas-knit, or modified atlas-knit tube.

5. A self-expanding endoluminal stent-graft according to claim 4, wherein:

said PET mesh is knitted from approximately seventy denier, approximately thirty-four filament, false twist fiber.

6. A self-expanding endoluminal stent-graft according to claim 5, wherein:

said PET mesh has a design with between one hundred and one thousand picks per squared inch.

7. A self-expanding endoluminal stent-graft according to claim 1, wherein:

said tubular deformable textile material is coated with a fibrous layer of polycarbonate urethane having a melting point lower than the melting point of said tubular deformable textile material, and said tubular deformable textile material is affixed to said self-expanding wire stent by melting said layer of polycarbonate urethane.

8. A self-expanding endoluminal stent-graft according to claim 1, wherein:

said self-expanding wire stent is coated with a fibrous layer of polycarbonate urethane having a melting point lower than the melting point of said tubular deformable textile material, and said tubular deformable textile material is affixed to said self-expanding wire stent by melting said layer of polycarbonate urethane.

9. A self-expanding endoluminal stent-graft according to claim 1, wherein:

said tubular deformable textile material is coated with a fibrous layer of polycarbonate urethane having a melting point lower than the melting point of said tubular deformable textile material, said self-expanding wire stent is coated with a fibrous layer of polycarbonate urethane having a melting point lower than the melting point of said tubular deformable textile material, and said tubular deformable textile material is affixed to said self-expanding wire stent by melting said layers of polycarbonate urethane.

10. A self-expanding endoluminal stent-graft according to claim 1, further comprising:

c) a non-woven elastic tube, wherein
said non-woven tube is arranged substantially coaxially with said self-expanding wire stent and said tubular deformable textile material is affixed to at least one of said self-expanding wire stent and said tubular deformable textile material.

11. A self-expanding endoluminal stent-graft according to claim 1, wherein:

said tubular deformable textile material is affixed to the interior of said self-expanding wire stent.

12. A self-expanding endoluminal stent-graft according to claim 10, wherein:

said tubular deformable textile material is affixed to the interior of said self-expanding wire stent, and said non-woven tube is affixed to the interior of said tubular deformable textile material.

13. A self-expanding endoluminal stent-graft according to claim 10, wherein:

said tubular deformable textile material is affixed to the interior of said self-expanding wire stent, and said non-woven tube is affixed to the exterior of said self-expanding wire stent.

14. A self-expanding endoluminal stent-graft according to claim 1, further comprising:

c) a second self-expanding wire stent, wherein
said tubular deformable textile material is affixed to the exterior of said self-expanding wire stent and said second self-expanding wire stent is affixed to the exterior of said tubular deformable textile material.

15. A self-expanding endoluminal stent-graft according to claim 14, further comprising:

d) a non-woven elastic tube, wherein
said non-woven tube is arranged substantially coaxially with said self-expanding wire stent and said tubular deformable textile material is affixed to one of said self-expanding wire stent and said tubular deformable textile material.

16. A self-expanding endoluminal stent-graft according to claim 15, wherein:

said tubular deformable textile material is affixed to the interior of said second self-expanding wire stent, and said non-woven tube is affixed to the interior of said tubular deformable textile material.

17. A self-expanding endoluminal stent-graft according to claim 1, wherein:

said tubular deformable textile material is made from approximately seventy denier PET fiber which is pulled through a bath containing polycarbonate urethane and braided on a braiding machine at an approximately 90° pick angle.

18. A self-expanding endoluminal stent-graft according to claim 1, wherein:

said tubular deformable textile material is made from approximately seventy denier PET fiber which is pulled through a bath containing polycarbonate urethane and wound with a-transversing shuttle onto a rotating mandril such that the angle at which the fiber crosses is approximately 45°.

19. A self-expanding endoluminal stent-graft according to claim 10, wherein:

said non-woven elastic tube is made from polycarbonate urethane spun on a mandril.

20. A self-expanding endoluminal stent-graft according to claim 1, wherein:

said self-expanding wire stent is coated with vulcanizing silicone rubber adhesive and said tubular deformable textile material is affixed to said self-expanding wire stent by curing said adhesive.

* * * * *